United States Patent [19]

Hartig et al.

[11] Patent Number: 4,491,637

[45] Date of Patent: Jan. 1, 1985

[54] COBALT-CONTAINING SUPPORTED CATALYSTS AND THEIR PREPARATION

[75] Inventors: Juergen Hartig, Gruenstadt; Armin Stoessel, Frankenthal; Guenter Herrmann, Heidelberg; Laszlo Marosi, Ludwigshafen, all of Fed. Rep. of Germany

[73] Assignee: BASF Aktiengesellschaft, Fed. Rep. of Germany

[21] Appl. No.: 499,354

[22] Filed: May 31, 1983

[30] Foreign Application Priority Data

Jun. 11, 1982 [DE] Fed. Rep. of Germany ....... 3222143

[51] Int. Cl.³ .......................... B01J 29/14; B01J 29/24
[52] U.S. Cl. .......................................... 502/66; 502/74
[58] Field of Search ............................. 502/66, 74, 79

[56] References Cited

U.S. PATENT DOCUMENTS

| | | | |
|---|---|---|---|
| 2,967,159 | 1/1961 | Gladrow et al. | 502/64 |
| 3,200,082 | 8/1965 | Breck et al. | 502/74 |
| 3,346,328 | 10/1967 | Sergeys et al. | 502/79 X |
| 3,783,123 | 1/1974 | Young | 502/79 X |
| 4,003,850 | 1/1977 | Callighan et al. | 502/74 |
| 4,070,403 | 1/1978 | Homeier | 502/74 X |

*Primary Examiner*—Carl F. Dees
*Attorney, Agent, or Firm*—Keil & Weinkauf

[57] ABSTRACT

Supported catalysts containing from 2 to 30% by weight, calculated as cobalt, of cobalt in oxidic form on a zeolite carrier, and their preparation.

4 Claims, No Drawings

COBALT-CONTAINING SUPPORTED CATALYSTS AND THEIR PREPARATION

The present invention relates to supported catalysts containing from 2 to 30% by weight, calculated as cobalt, of cobalt in oxidic form.

In the oxidation of cyclohexane with air or oxygen under superatmospheric pressure and at elevated temperatures, a mixture of cyclohexanol, cyclohexanone, cyclohexyl hydroperoxide, acids and esters is obtained. To improve the yield, the hydroperoxide formed is usually decomposed in the presence of a homogeneous solution of a metal salt, e.g. a cobalt or chromium salt, as disclosed in German Pat. No. 1,002,754. Copper and manganese salts have also been used for this purpose, as disclosed in German published application DAS 1,193,501.

Supported catalysts have also been used for the decomposition of mixtures containing cyclohexyl hydroperoxide. U.S. Pat. No. 2,851,496 describes metals of group 8, inter alia cobalt oxide, on active aluminum oxide, carbon, silica gel or kieselguhr as being suitable catalysts. However, the literature (German Laid-Open application DOS No. 2,352,378) discloses that the conversion rate is low and the catalyst demand high.

Similar deficiencies are found when the reaction is carried out at elevated temperatures as disclosed in Kogyo Kagaku Shashi, 73 (1970), 2,056 et seq. Although the higher temperatures result in an increased reaction velocity, the yield is reduced owing to thermal decomposition of the peroxide at the stated temperatures.

German Laid-Open application DOS No. 2,352,378 states that heterogeneous chromium oxide catalysts are used for the decomposition of cyclohexyl hydroperoxide. In respect of their service life and sensitivity to water, however, these catalysts do not satisfy the industrial requirements.

It is an object of the present invention to provide a catalyst for the conversion of cyclohexyl hydroperoxide to cyclohexanone and cyclohexanol, which catalyst gives a high yield and high conversion and furthermore has a long service life and is substantially stable to water.

We have found that this object is achieved by a supported catalyst containing from 2 to 30% by weight, calculated as the metal, of cobalt in oxidic form, wherein the carrier used is a zeolite.

The present invention also relates to the preparation of the above supported catalysts by a process wherein an A, X or Y zeolite is suspended in water, an aqueous solution of a cobalt salt is added at from 40° to 100° C. while maintaining a pH of from 7.5 to 12, and the product is isolated from the aqueous solution, dried, and sintered at from 200° to 600° C.

The novel catalysts have the advantages that they possess a long service life and are substantially stable to water, that the active catalytic metal is eluted to only a small extent, and that the decomposition of cyclohexyl hydroperoxide to cyclohexanol and cyclohexanone takes place with high yields and conversions.

The catalysts according to the invention contain from 2 to 30, preferably from 10 to 25, % by weight, calculated as cobalt, of cobalt in oxidic form. The percentages are based in each case on the total material comprising the carrier and the active catalytic metal. It has also been found to be useful if the catalyst contains from 3 to 16% by weight, calculated as sodium, of sodium in bound form. The catalytically active cobalt is applied onto a zeolite carrier, and A, X and Y zeolites have proved particularly suitable. Preferably, the catalytically active cobalt is incorporated into the zeolite structure. To achieve better moldability of the catalyst material during the preparation of the catalyst, it has also proved useful to add, before molding, for example not more than 35% by weight of active aluminum oxide or hydroxide, e.g. boehmite, as a binder. In this case, the above percentages are based on the total material comprising the active catalytic metals, the zeolite and the binder.

Suitable catalysts are obtained, for example, by precipitating a cobalt compound from aqueous solution onto a zeolite, the cobalt compound used being capable of conversion to its oxide on heating. Advantageously, an aqueous solution of a cobalt salt, e.g. cobalt sulfate, cobalt nitrate or cobalt acetate, is used, and precipitation is carried out by adding an alkali metal hydroxide or carbonate solution. It has proved advantageous to maintain, during precipitation, a pH of from 7.5 to 12, in particular from 8 to 11. As a rule, precipitation is carried out at from 40° to 100° C. The resulting zeolite carrier containing cobalt hydroxide and/or cobalt carbonate is then advantageously washed with water, expediently with water containing an alkali, e.g. a 0.1–0.5% strength by weight sodium hydroxide solution if the ready-prepared catalyst is to have a particular sodium content. The supported catalyst thus obtained is advantageously dried at from 100° to 150° C., for example for from 1 to 20 hours, and is then sintered at from 200° to 600° C., for example for from 2 to 8 hours. As a rule, sintering is carried out in the presence of a gas containing molecular oxygen, e.g. air.

It has proved useful, if the catalyst is to be converted to moldings, to add, for example, not more than 35% by weight of active aluminum oxide or hydroxide, e.g. boehmite, as a binder, before calcination, and to convert the resulting mixture to moldings. The moldings thus obtained are then sintered as described above.

It is assumed that cobalt is present in the form of its oxide, although it is not always possible to carry out an X-ray analysis to establish this. It is also possible that partial ion exchange with the zeolite takes place during the preparation.

In addition to the above, preferred method of preparing the catalysts employed, it is also possible to obtain the ready-prepared catalysts by applying the metal compounds by impregnation or spraying, and following this procedure by heating.

The catalysts according to the invention are used for the preparation of cyclohexanone and cyclohexanol from cyclohexyl hydroperoxide. Advantageously, a solution of cyclohexyl hydroperoxide in cyclohexane is employed, a suitable solution containing, for example, from 0.5 to 10% by weight of cyclohexyl hydroperoxide. It is particularly preferable to employ a mixture obtained by oxidation of cyclohexane with molecular oxygen or a gas containing this, e.g. air, in the liquid phase at from 130° to 200° C. and under a pressure of from 5 to 25 bar, in the presence or absence of a catalyst. Advantageously, the resulting reaction mixture is washed with water, an alkali metal carbonate solution or a caustic alkali solution before being subjected to further treatment. A typical reaction mixture contains, in addition to cyclohexane, from 1 to 7% by weight of cyclohexanone and cyclohexanol and from 0.5 to 5% by weight of cyclohexyl peroxide, as well as byproducts, such as esters. The reaction mixture may furthermore contain water, for example in an amount of not more than 2% by weight. Suitable reaction mixtures are obtained, for example, by the process described in German Pat. No. 1,046,610.

The treatment of the cyclohexyl hydroperoxide, or of a solution containing this, with the novel catalyst is advantageously carried out at from 40° to 160° C., in particular from 80° to 120° C., and under atmospheric pressure or slightly superatmospheric pressure, for example as employed in the oxidation of cyclohexane, e.g. not more than 20 bar. The cyclohexyl hydroperoxide-containing solution or reaction mixture is advantageously treated continuously by passing such a solution or mixture over a fixed-bed catalyst. If the activity of the catalyst diminishes after a relatively long operating time, the catalyst can be readily reactivated by treatment with a gas containing molecular oxygen, in particular air, for example at from 150° to 500° C.

The Examples which follow illustrate the invention.

EXAMPLE 1

(a) Preparation of the catalyst 1,455 g of $Co(NO_3)_2.6H_2O$ are dissolved in 1,000 g of distilled water, and this solution is added to 500 g of zeolite 4A. The aqueous phase is evaporated off in a rotary evaporator under reduced pressure from a water-pump and at a water bath temperature of about 95°–100° C., this procedure being carried out until the catalyst is dry. It is then ground, and calcined for 3 hours. The catalyst then contains 26.6% by weight of Co and 7.8% by weight of Na, and an aqueous suspension of the catalyst has a pH of 9.8 (catalyst I).

To prepare extrudates, the catalyst powder is mixed with boehmite (AlO(OH)), and the mixture is kneaded for half an hour without peptization, and then converted to 4 mm extrudates. These are then calcined once again for 3 hours at 300° C. The ready-prepared catalyst (II) has the following composition: 8% by weight of Co, 5.3% by weight of Na, 23.2% by weight of Al, 0.5% by weight of $NO_3$, remainder Si and O.

(b) Decomposition of cyclohexyl hydroperoxide

In a stirred flask provided with an internal thermometer and a reflux condenser, 2.0 g of the above catalyst powder (I) are stirred for 30 minutes at 80° C. with 100 g of a mixture obtained by oxidizing cyclohexane with air at 145° C. and under 12 bar (composition: 1.81% of cyclohexanone, 2.61 % of cyclohexanol, 1.48% of cyclohexyl hydroperoxide, remainder cyclohexane and by-products, such as carboxylic acids and carboxylates). Gas chromatographic analysis of the product gives the following composition: 2.31% of cyclohexanone, 3.15% of cyclohexanol and 0.38% of cyclohexyl hydroperoxide. The yield of cyclohexanone and cyclohexanol is 119%, based on a peroxide conversion of 74%.

COMPARATIVE EXAMPLE 1

728 g of $Co(NO_3)_2.6H_2O$ are dissolved in 500 ml of distilled water, and 500 ml of 4 mm active carbon extrudates are added to this solution. The supernatant solution is distilled off, and the catalyst is dried at 100° C. in a drying oven. The impregnating process is repeated 5 times, after which the total amount of Co has been applied. The extrudates are dried at from 100° to 110° C., and then calcined in a muffle furnace at 300° C., under an $N_2$ atmosphere. The ready-prepared catalyst contains 32.6% by weight of Co. 2.0 g of the catalyst are milled, and stirred with 100 g of the oxidation mixture described in Example 1(b) for 30 minutes at 80° C. The peroxide conversion is 94%, and the yield of cyclohexanone and cyclohexanol is only 87%.

EXAMPLE 2

200 ml (150 g) of the catalyst II are introduced into a glass tube which has an internal diameter of 30 mm and a length of 400 mm and is provided with a jacket and an internal thermocouple. The feed mixture is pumped through the catalyst from below, at a constant rate and at 80° C., which is maintained by the heating fluid circulating in the jacket. The feed mixture is obtained from the oxidation of cyclohexane with air, and contains, in addition to cyclohexane, 1.64% by weight of cyclohexanone, 2.40% by weight of cyclohexanol, 1.47% by weight of cyclohexyl hydroperoxide, 0.06% by weight of other peroxides, and 0.9 meq/liter of acids and carboxylates. The reacted mixture is analyzed from time to time. The effective residence time, based on the dead space, is 18.5 minutes.

| Time-on-stream (h) | Peroxide conversion+ (%) | Cyclohexyl hydroperoxide++ conversion (%) | Yield (%) based on conversion |
|---|---|---|---|
| 32 | 91 | 100 | 129 |
| 127 | 90 | 100 | 121 |
| 215 | 90 | 100 | 119 |
| 295 | 90 | 100 | 121 |
| 335 | 90 | 100 | 121 |
| 402 | 90 | 100 | 119 |
| 508 | 90 | 99 | 118 |

After 508 hours' time-on-stream, the catalyst is completely unchanged and does not exhibit any scaling or substantial loss of activity.

COMPARATIVE EXAMPLE 2

200 ml (110 g) of the Co/ carbon catalyst from Comparative Example 1 are introduced into the experimental apparatus described in Example 2, and the oxidation mixture is treated as described in Example 2. The following values are obtained.

| Time-on-stream (h) | Peroxide conversion+ (%) | Cyclohexyl hydroperoxide++ conversion (%) | Yield (%) based on conversion |
|---|---|---|---|
| 24 | 98 | 100 | 102 |
| 56 | 96 | 100 | 100 |
| 102 | 91 | 98 | 98 |
| 184 | 85 | 97 | 93 |

+Conversion based on the peroxides present in the product mixture
++Conversion based on cyclohexyl hydroperoxide in the product mixture

EXAMPLE 3

(a) Preparation of the catalyst 50 g of zeolite A are suspended in 2 liters of water, the suspension is heated to 80° C. and the pH is brought to 10.5–11 with sodium hydroxide solution. A solution of 195 g of $Co(NO_3)_2.6H_2O$ in 300 ml of water is added to this suspension in the course of 1 to 2 hours, the above-mentioned pH being maintained by simultaneous addition of a solution of 35 g of sodium hydroxide in 300 ml of water. When the addition is complete, the mixture is brought to 100° C. and then cooled to 60°–70° C., after which the precipitate is filtered off and washed with 1,500 ml of water whose pH has been brought to about 8 by the addition of sodium hydroxide solution. Thereafter, the filter cake is dried for 18 hours at 120° C. and then heated for 3 hours at 300° C. The catalyst thus obtained contains 24.5% by weight of cobalt, 6.8% by weight of sodium and 0.5% by weight of nitrate.

(b) Decomposition of cyclohexyl hydroperoxide

In an autoclave, 100 g of a solution of 2.0% by weight of cyclohexyl hydroperoxide and 2.0% by weight of cyclohexanone in cyclohexane are heated together with 2.0 g of the above catalyst for 30 minutes at 80° C., while stirring. Thereafter, the catalyst is filtered off, washed with cyclohexane and used repeatedly. The filtrate obtained each time is analyzed for cyclohexanone, cyclohexanol and cyclohexyl hydroperoxide. The results are summarized below. After the catalyst has been used for the third time, 0.03 ppm of cobalt is detectable in the products.

| Experiment | Peroxide conversion (%) | Yield (%) (based on conversion) |
|---|---|---|
| 1 | 68 | 118 |
| 2 | 68 | 117 |
| 3 | 68 | 118 |

We claim:
1. A supported catalyst containing from 2 to 30% by weight, calculated as cobalt, of cobalt in oxidic form, and from 3 to 16% by weight, calculated as the metal, of sodium in bound form, wherein the carrier used is zeolite.
2. A supported catalyst as set forth in claim 1, wherein the carrier is an A, X or Y zeolite.
3. A process for the preparation of a supported catalyst containing from 2 to 30% by weight, calculated as cobalt, of cobalt in oxidic form and from 3 to 16% by weight, calculated as the metal, of sodium in bound form, which process comprises suspending an A, X or Y zeolite in water; adding to the suspension a cobalt salt solution at a temperature of from 40° to 100° C. while maintaining a pH of 8 to 11; isolating the product from the aqueous solution; washing the product with an aqueous solution of 0.1 to 0.5% by weight of sodium hydroxide; and thereafter drying and calcining the product at from 200° to 600° C.
4. A supported catalyst as set forth in claim 1 which contains from 10 to 25% by weight of cobalt in oxidic form.

* * * * *